(12) United States Patent
Kelley et al.

(10) Patent No.: US 8,062,872 B2
(45) Date of Patent: Nov. 22, 2011

(54) METHODS AND COMPOSITIONS FOR OPTIMIZING FERMENTATION

(75) Inventors: Douglas G. Kelley, Wenatchee, WA (US); Richard A. Handley, Loon Lake, WA (US)

(73) Assignee: Inland Environmental Resources, Inc., Pasco, WA (US)

( * ) Notice: Subject to any disclaimer, the term of this patent is extended or adjusted under 35 U.S.C. 154(b) by 741 days.

(21) Appl. No.: 11/933,600

(22) Filed: Nov. 1, 2007

(65) Prior Publication Data

US 2009/0053785 A1 Feb. 26, 2009

Related U.S. Application Data

(60) Provisional application No. 60/863,927, filed on Nov. 1, 2006.

(51) Int. Cl.
*C12P 7/10* (2006.01)
(52) U.S. Cl. ............... 435/165; 435/41; 435/161
(58) Field of Classification Search .......... None
See application file for complete search history.

(56) References Cited

U.S. PATENT DOCUMENTS

| | | | |
|---|---|---|---|
| 2,272,982 A | 2/1942 | Owen | |
| 2,685,554 A | 8/1954 | Darken et al. | |
| 3,933,788 A | 1/1976 | Kang et al. | |
| 3,963,637 A | 6/1976 | Chappell | |
| 4,415,467 A | 11/1983 | Piepho | |
| 4,566,986 A | 1/1986 | Waldmann | |
| 4,812,410 A | 3/1989 | Lawford | |
| 4,870,010 A * | 9/1989 | Hayes | 424/114 |
| 4,877,524 A | 10/1989 | Eberhardt | |
| 4,999,195 A * | 3/1991 | Hayes | 424/114 |
| 5,487,989 A | 1/1996 | Fowler et al. | |
| 6,203,722 B1 | 3/2001 | Hurst | |
| 6,383,398 B2 | 5/2002 | Amer | |
| 6,589,427 B2 | 7/2003 | Moghe et al. | |
| 6,929,759 B2 | 8/2005 | Fruh et al. | |
| 7,102,057 B2 | 9/2006 | Lanahan et al. | |
| 7,108,792 B2 | 9/2006 | Wegner | |
| 7,445,718 B2 | 11/2008 | Misra et al. | |
| 2003/0213753 A1 | 11/2003 | Landis et al. | |

OTHER PUBLICATIONS

Osman et al "Mechanism of Ethanol Inhibition of Fermentation in *Zymomonas mobilis* CP4" Oct. 1985 Journal of Bacteriology, p. 173-180.*

\* cited by examiner

*Primary Examiner* — Herbert J. Lilling
(74) *Attorney, Agent, or Firm* — Richard T. Black; Foster Pepper PLLC

(57) ABSTRACT

Embodiments described include methods for maintaining the pH and alkalinity during industrial fermentation processes are described that foster optimal microorganism activities throughout the duration of the fermentation process. Magnesium based buffering agents having sufficient buffering capacity and applied at sufficient concentration levels required to neutralize the acidic content of fermentation fluids during the fermentation process cycle are detailed. These magnesium based buffering agents control fermenter processes without causing extreme pH swings to maximize the production of desired fermentation products.

16 Claims, No Drawings

METHODS AND COMPOSITIONS FOR OPTIMIZING FERMENTATION

RELATED APPLICATIONS

This application incorporates by reference in its entirety and claims priority to U.S. Provisional Patent Application Ser. No. 60/863,927 filed Nov. 1, 2006.

BACKGROUND OF THE INVENTION

Academic literature has taught that by controlling the pH of fermentations at or near the optimum pH for the primary fermentation microorganism, the concentration of the desired fermentation product is enhanced. For instance, by fixing the pH of a corn mash fermentation at 5.0-5.5, which is optimum for yeast, the yield of ethanol is enhanced. Use of strong alkalis, such as NaOH or KOH, can result in pH swings high or low that can cause a significant reduction in fermentation performance.

The fermentation process for converting an organic substrate into simpler organic chemicals, such as the conversion of glucose in corn mash into ethanol and carbon dioxide, is accomplished through microbiological activity. Microorganisms perform the functions of fermentation optimally under a narrow window of temperature, pH, and nutrient conditions. There are many types of industrial fermentation processes, such as fuel ethanol production, sewage digestion, the making of bread, beer, wine, and cheese, and pharmaceutical applications to produce important chemicals, such as vancomycin, paclitaxel, insulin lispro. Each industrial fermentation requires different conditions for optimum yield of desired products.

When a particular microorganism is introduced into a selected growth medium, growth in the population of the microorganism does not occur immediately. This period of adaptation is called the lag phase. The lag phase is followed by the exponential growth phase, where the rate of growth of the microorganism steadily increases. Toward the end of the exponential growth phase, the rate of growth slows down, due to the continuously falling concentrations of nutrients and/or continuously increasing concentrations of by-products that are toxic to the microorganism. During this deceleration phase the rate of growth is slowed and then ceases. Unless other microorganisms contaminate the culture, the biomass remains constant and the chemical constitution remains unchanged.

It is a goal of industrial fermentations to increase the exponential growth rate or to prolong the time during which the microorganisms are performing at an exponential growth rate. In so doing, the final yield of a desired fermentation product will be increased. For instance, in the fuel ethanol industry, the ability to provide a consistent measurable increase in the final percent ethanol concentration from corn mash fermentations may translate into a significant increase in the profitability of the overall process.

A current challenge in the fuel ethanol industry is the build up of contaminants that are inhibitory to the performance of the yeast. The increase in the concentration of acetic acid and lactic acid from inhibitory bacteria present in the corn mash fermentation result in a decrease in the yeast (*Saccharomyces cerevisiae*) growth rate, resulting in decreased ethanol production. *Lactobacillus* and *Acetobacter* are commonly occurring bacterial contaminants in ethanol fermentations that produce lactic acid and acetic acid inhibitory by-products. A study by Ingledew in 2001 (J. Ind. Microbiol. Biotechnol. 2001 March; 26(3): 171-7) showed that the specific growth rates of certain *Saccharomyces cerevisiae* strains decreased exponentially with the increase of acetic acid or lactic acid concentrations in minimal media at 30° C. Furthermore, the lag phase increase displayed in the growth curves increased exponentially with the increasing acetic acid or lactic acid concentrations. However, a very recent study by Narendranath in 2006 (J. Ind. Microbiol. Biotechnol. 2006 June; 33(6): 469-74) concluded the ethanol production experienced inhibitory effects attributed lactic acid and/or acetic acid concentrations in corn mash fermentation broths could be mitigated when a pH range of approximately 5.0-5.5 was attained in the corn mash. The inhibitory effects were also mitigated in other fermentation solutions, for example, laboratory media. In this study, fermentations were performed at fixed pH values of 4.0, 4.5, 5.0, and 5.5, with dramatic inhibitory effects being observed at pH 4.0 and mild inhibitory effects at pH 5.5. The method for fixing the pH of these laboratory corn mash fermentations was to adjust the pH using 8 M potassium hydroxide (KOH), a strong base, and concentrated sulfuric acid ($H_2SO_4$), a strong acid.

For industrial fermentation purposes, the use of a strong acid or a strong base to maintain the pH of a selected growth medium would require very stringent chemical feed control. A slight overdose of either the strong acid or strong alkali into a fermenter could result in a significant departure from the desired pH range for microorganism activity, which would decrease the yield of the desired fermentation product. A significant overdose of a strong acid or base into a fermenter could cause a complete stoppage of the fermentation process altogether.

SUMMARY OF THE PARTICULAR EMBODIMENTS

Embodiments of the invention include compositions of and methods for using a magnesium based buffering agent or magnesium based buffering agents to establish pH control in industrial and lab scale fermentations without causing wide swings in acidity and alkalinity levels.

DETAILED DESCRIPTIONS OF THE PARTICULAR EMBODIMENTS

Embodiments described herein are directed generally to magnesium based formulations and methods of using effective amounts of magnesium base formulations in maintaining the pH of industrial and smaller scale fermentations to increase the yield of desired products. More particularly, the methods for maintaining fermenter pH may be tailored to or optimized for specific microorganism activity during the fermentation process by utilizing effective amounts of magnesium based buffering agents as needed to achieve desired fermenter pH ranges. The effective amounts of magnesium based buffering agents needed depends on the acidity, alkalinity, and/or other constituents present in the fermentation media and the mass action levels presented by the acids, bases, and other constituents initially present at the beginning of the fermentation process or changes in the mass action levels or concentrations that occur during fermentation.

Other embodiments provide for adding the effective amounts to attain or restore desired pH ranges by the adding of magnesium based agents or agents to fermenter broths or microbe/broth mixtures either in batch wise, continuous, and/ or batch wise and continuous at sufficient liquid concentrations or by adding sufficient solid magnesium based formulations so that effective level of the magnesium buffering agent is operational within the fermenter broth or fermenter broth/microbe mixture. The batch wise and/or continuous addition of magnesium based formulations discussed below may be added throughout the duration of the fermentation in order to maximize production of the desired fermentation product by adding to the fermenter the sufficient amount of a magnesium based buffering agent to attain and maintain the desired pH range.

Other embodiments described herein are directed generally to adjusting the pH of industrial fermentations and more particularly to methods for adjusting the pH and alkalinity during an industrial fermentation process at a time when the fermentation is beginning to show signs of reduced production or increases in inhibitory by-products. In these cases, the pH conditions are adjusted using effective amounts of the magnesium formulations to optimize the yeast microorganism activity throughout the remainder of the fermentation. The pH conditions are adjusted in order to maximize production of the desired fermentation product by adding to the fermenter sufficient amounts of the magnesium based buffering agent or magnesium based buffering agents.

Since the pH of industrial fermentations naturally trends to lower levels, due to the generation of carbon dioxide and the presence of acid-producing bacterial contaminants, there is a need in the industry for a mild but strong alkaline buffering agent that can be fed into batch or continuous fermentations for the purpose of controlling the pH at a desired level throughout the duration of a fermentation, or to bring the pH of the fermentation to a desired level to optimize yeast performance for the remainder of a fermentation.

Other embodiments including methods for maintaining the pH and alkalinity during industrial fermentation processes are described that foster optimal microorganism activities throughout the duration of the fermentation process. Magnesium based buffering agents having sufficient buffering capacity and applied at sufficient concentration levels as required to neutralize the acidic content of fermentation fluids during the fermentation process cycle are described below. These magnesium based buffering agents control fermenter processes without causing extreme pH swings to maximize the production of the desired fermentation products.

The magnesium based buffering agent used to maintain the pH and alkalinity for fermentation may include, for example magnesium oxide, magnesium hydroxide, or mixtures of these. The magnesium based buffering agent may additionally contain at least one or more of the following additional alkalinity supplementing agents: calcium oxide, calcium hydroxide, dolime, ammonia, sodium hydroxide, sodium carbonate, sodium bicarbonate, potassium hydroxide, potassium carbonate, alkaline phosphate salts, alkaline pyrophosphate salts, alkaline polyphosphate salts, and mixtures of these. Preferably, magnesium hydroxide will be employed as the magnesium based buffering agent, since it possesses very strong buffering capacity, as well inherent insolubility under conditions of overfeed. The insolubility of magnesium hydroxide under overfeed conditions will not result in a pH spike that can significantly damage the course of the fermentation. Rather, an overfeed of magnesium hydroxide will only incorporate insoluble $Mg(OH)_2$ into the nutrient and biosolids matrix present in the fermenter, and will only result in a gentle pH increase and maximum buffering capacity.

There could be circumstances in which the product yield from fermentation will be further enhanced by feeding a second chemical formulation into the fermenter, but in unison with, the magnesium based buffering agent, or separately just prior to the fermentation, where the second chemical formulation include those which contain at least one compound selected from the group consisting of calcium oxide, calcium hydroxide, dolime, ammonia, sodium hydroxide, sodium carbonate, sodium bicarbonate, potassium hydroxide, potassium carbonate, alkaline phosphate salts, alkaline pyrophosphate salts, alkaline polyphosphate salts, and mixtures of these. Addition of a second chemical formulation along with the magnesium based buffering agent may allow for a more rapid pH increase at times during a fermentation when the pH has fallen to a very low level. Addition of a second chemical formulation along with the magnesium based buffering agent may provide both alkalinity and nutrients for optimizing the microbiological activity of the product yielding microorganism. For instance, the supplemental addition of ammonia along with magnesium hydroxide may provide strong and gentle buffering to optimize the pH range, while at the same time providing additional nitrogen as a nutrient.

The desired location for feed of the magnesium based buffering agent is directly into the digester, in order to initiate the fermentation at the optimum pH for the primary active microorganism, and to maintain the pH during the entire extent of the fermentation at or near the optimum pH for the primary active microorganism.

Alternatively, the magnesium based buffering agent could be fed into the nutrient-rich feed stock stream just prior to microorganism inoculation of the fermenter to boost the overall pH and alkalinity of the feed stock as it enters the fermenter (just prior to fermentation). This allows increased contact time for the magnesium based buffering agent to release a maximum buffering strength to the feed stock so that the fermentation process may be initiated at the optimum pH and alkalinity.

The desired feeding method is to use an automated pH probe and controller that activates a metering pump. In this way, any downward drift in pH will be immediately monitored and automatically adjusted. The downside of this approach is that the pH probe, if left unattended, may foul and provide erroneous readings. This approach will work effectively if operator time is dedicated to monitor and calibrate the probe on a regular, perhaps hourly, basis.

A manual monitoring and feed method may also be employed by performing grab sample pH monitoring of the fermentation process over time, whereby additional doses of the magnesium based buffering agent can be applied directly into the fermenter as needed.

With either the automated or manual magnesium based buffering agent feed approaches, the strategy should be to maintain the pH within a range that straddles the optimum pH for activity of the selected microorganism. For instance, for the fuel ethanol industry, the optimum pH for yeast (*Saccharomyces cerevisiae*) growth rate in a corn mash is between 5.0 and 5.5. Therefore, one strategy would be to add the magnesium buffering agent or agents into the corn mash as it enters the fermenter so that the initial pH of the fermentation is at 5.5. After the fermentation has had time to develop a significant ethanol production rate and the pH has dropped to 5.0, add a second dose of the magnesium containing buffering agent to bring the pH back to 5.5. Then, throughout the remainder of the fermentation, the pH is maintained within the range of 5.0 to 5.5 in this way.

By using magnesium oxide or magnesium hydroxide as the magnesium based buffering agent, an accidental overfeed of the buffering agent will not cause a dramatic pH spike that could cause a large decrease in the performance of the primary microorganism in the fermentation. This benefit of the use of magnesium oxide or magnesium hydroxide is unique as compared to more caustic alkaline chemicals, such as sodium hydroxide and potassium hydroxide.

Alternate composition embodiments of the formulations may also include dispersants. The suitable dispersants include, for example, any single or combination of polymeric anionic dispersants and salts thereof including homopolymers, copolymers and/or terpolymers having acid functionalities and any one or more monomers of maleic acid, maleic anhydride, acrylic acid, methacrylic acid, crotonic acid, itaconic acid, mesaconic acid, fumaric acid, vinylphosphonic acid, vinylsulfonic acid citraconic acid, vinylacetic acid, acryloxypropionic acid, vinylsulfonic acid, styrenesulfonic acid, 2-acrylamido-2-methylpropanesulfonic acid, allylsulfonic acid, allylphosphonic acid, vinylphosphonic acid, vinylsulfonic acid, acrylic acid and methacrylic acid.

Other alternate composition embodiments of formulations may also include viscosity-modifying agents. The suitable viscosity modifying agents include, for example, any single or combination of calcium oxide, calcium hydroxide, formic acid, acetic acid, propionic acid and butyric acid and salts thereof. Other embodiments may include mannitol, mono-, di- and trisaccharides, including sucrose and lactose, and any manufacturing byproducts containing sugar-based organics substances as viscosity modifying agents. Other solution embodiments may include formic acid, acetic acid, propionic acid, butyric acid HCl, $HNO_3$, $HClO_4$, and aluminum, ferric, magnesium, calcium and barium salts thereof as viscosity modifying agents. Yet other embodiments may include calcium acetate, magnesium acetate and mixtures thereof as viscosity modifying agents.

While the particular embodiments of the invention have been illustrated and described, as noted above, many changes can be made without departing from the spirit and scope of the invention. Accordingly, the scope of the invention is not limited by the disclosure of the particular embodiments. Instead, the invention should be determined entirely by reference to the claims that follow.

We claim:

1. A method for increasing the product yield of a fermentation process comprising:
   defining the primary active microorganism of the fermentation process;
   selecting a desired pH range for the primary active microorganism to be achieved in a fermenter broth or a fermenter microbe/broth mixture; and
   applying continuously to the fermenter broth or the fermenter microbe/broth mixture a sufficient amount of a magnesium based buffering agent formulated to have at least one of magnesium oxide and magnesium hydroxide to attain the desired pH range throughout the duration of the fermentation process.

2. The method of claim 1, wherein selecting the desired pH range of the fermentation process is determined by the pH range that fosters maximal activity of the primary microorganism used in the fermentation process.

3. The method of claim 2, wherein selecting the desired pH range is that which fosters maximal activity of yeast for fuel ethanol production.

4. The method of claim 1, wherein selecting the desired pH range includes the fermentation process being approximately between pH 4.5 and pH 6.0.

5. The method of claim 4, wherein selecting the desired pH range includes the fermentation process between approximately pH 5.0 and pH 5.5.

6. The method of claim 1, wherein applying continuously further includes applying batch wise to the fermenter broth or fermenter broth/microbe mixture to maintain the desired pH range.

7. The method of claim 1, wherein the magnesium based buffering agent is further formulated with at least one additional compound selected from the group consisting of calcium oxide, calcium hydroxide, dolime, ammonia, sodium hydroxide, sodium carbonate, sodium bicarbonate, potassium hydroxide, potassium carbonate, alkaline phosphate salts, alkaline pyrophosphate salts, alkaline polyphosphate salts, and mixtures thereof.

8. The method of claim 1, wherein a second chemical formulation is fed separately, but in unison with, the magnesium based buffering agent, where the second chemical formulation contains at least one compound selected from the group consisting of calcium oxide, calcium hydroxide, dolime, ammonia, sodium hydroxide, sodium carbonate, sodium bicarbonate, potassium hydroxide, potassium carbonate, alkaline phosphate salts, alkaline pyrophosphate salts, alkaline polyphosphate salts, and mixtures thereof.

9. A method for increasing the ethanol yield of a fermentation process comprising:
   defining the primary active microorganism of the fermentation process;
   selecting a desired pH range for the primary active microorganism to be achieved in a fermenter broth or a fermenter microbe/broth mixture; and
   applying batch wise to the fermenter broth or the fermenter microbe/broth mixture a sufficient amount of a magnesium based buffering agent formulated to have at least one of magnesium oxide and magnesium hydroxide to the fermentation process to attain and maintain the desired pH range throughout the duration of the fermentation process.

10. The method of claim 9, wherein selecting the desired pH range of the fermentation process is determined by the pH range that fosters maximal activity of the primary microorganism used in the fermentation process.

11. The method of claim 10, wherein selecting the desired pH range includes that which fosters maximal activity of the primary microorganism fermented for fuel ethanol production.

12. The method of claim 10, wherein selecting the desired pH range includes the fermentation process being approximately between pH 4.5 and pH 6.0.

13. The method of claim 10, wherein selecting the desired pH range includes the fermentation process being approximately between pH 5.0 and pH 5.5.

14. The method of claim 9, wherein applying the magnesium based buffering agent further includes applying continuously to the fermenter broth or fermenter broth/microbe mixture to maintain the desired pH range.

15. The method of claim 9, wherein the magnesium based buffering agent is further formulated with at least one additional compound selected from the group consisting of calcium oxide, calcium hydroxide, dolime, ammonia, sodium hydroxide, sodium carbonate, sodium bicarbonate, potassium hydroxide, potassium carbonate, alkaline phosphate salts, alkaline pyrophosphate salts, alkaline polyphosphate salts, and mixtures thereof.

16. The method of claim 9, wherein a second chemical formulation is fed separately from the magnesium based buffering agent, the second chemical formulation comprising at least one compound selected from the group consisting of calcium oxide, calcium hydroxide, dolime, ammonia, sodium hydroxide, sodium carbonate, sodium bicarbonate, potassium hydroxide, potassium carbonate, alkaline phosphate salts, alkaline pyrophosphate salts, alkaline polyphosphate salts, and mixtures thereof.

* * * * *